(12) United States Patent
McKinney

(10) Patent No.: US 11,680,066 B2
(45) Date of Patent: Jun. 20, 2023

(54) IBOGAINE-RELATED COMPOUNDS AND CORRESPONDING METHODS

(71) Applicant: Jeffrey Alan McKinney, Half Moon Bay, CA (US)

(72) Inventor: Jeffrey Alan McKinney, Half Moon Bay, CA (US)

( * ) Notice: Subject to any disclaimer, the term of this patent is extended or adjusted under 35 U.S.C. 154(b) by 0 days.

(21) Appl. No.: 17/300,293

(22) Filed: May 13, 2021

(65) Prior Publication Data
US 2021/0371423 A1    Dec. 2, 2021

Related U.S. Application Data

(60) Provisional application No. 63/101,848, filed on May 18, 2020.

(51) Int. Cl.
| | |
|---|---|
| *A61K 31/55* | (2006.01) |
| *A61P 25/22* | (2006.01) |
| *A61P 25/30* | (2006.01) |
| *C07D 471/18* | (2006.01) |

(52) U.S. Cl.
CPC ........ *C07D 471/18* (2013.01); *C07B 2200/05* (2013.01)

(58) Field of Classification Search
CPC .......... A61K 31/55; A61P 25/22; A61P 25/30; C07D 471/18; C07B 2200/05
See application file for complete search history.

(56) References Cited

U.S. PATENT DOCUMENTS

| | | | |
|---|---|---|---|
| 6,211,360 B1 * | 4/2001 | Glick .................. | C07D 487/22 540/477 |
| 6,780,871 B2 | 8/2004 | Glick et al. | |
| 9,592,239 B2 | 3/2017 | Maillet | |

OTHER PUBLICATIONS

Seltzman et al., Metallation/Reduction as a New Approach to Tritium Labeling. The Synthesis of [3H]Ibogaine, Journal of Labelled Compounds and Radiopharmaceuticals, vol. 34, No. 4, pp. 367-375 (Year: 1994).*
Agwada et al., Die Alkaloide von Gabunia eglandulosa STAFF, Helvetica Chimica Acta, vol. 58 No. 4, pp. 1001-1006 (Year: 1975).*
CAS printout of Hootele et al., 19-Oxoconopharyngine from Conopharyngia jollyana, Chimia, vol. 22, No. 5, pp. 245-246 (Year: 1968).*
CAS printout of Hootele et al., Structural Correlation of 20-hydroyconopharyngine With Ibogaline, Bulletin des Societes Chimiques Beiges, vol. 21, No. 3, pp. 133-134 (Year: 1967).*
Buchi et al., Chemical Transformations of Ibogaine, Journal of the American Chemical Society, vol. 88, No. 11, pp. 2532-2535 (Year: 1966).*
Thomas et al., Thermal Methyl Transfer. The Mass Spectrum of Voacamine-d$\wedge$1, Journal of the American Chemical Society, vol. 87, No. 23, pp. 5447-5452 (Year: 1965).*
Biemann et al., Mass Spectrometric Evidence for the Structure of Iboxygaine and Its Tosylate, Tetrahedron Letters, vol. 2, No. 2, pp. 68-71 (Year: 1961).*

* cited by examiner

*Primary Examiner* — Brenda L Coleman
(74) *Attorney, Agent, or Firm* — Jeffrey A. McKinney; McKinney Law Group APC

(57) ABSTRACT

The present invention relates to Ibogaine derivatives and related methods. It more specifically relates to deutero- and fluoro-derivatives of Ibogaine and related methods. In one aspect, the present invention provides a compound. The structure of the compound is shown as compound 1 in FIG. 1. In another aspect, the present invention provides a method of treating an addiction disorder. The method comprises administration of compound 1. In another aspect, the present invention provides a method of treating an anxiety-related disorder or impulse control disorder. The method comprises administration of compound 1.

3 Claims, 6 Drawing Sheets

IBOGAINE-RELATED COMPOUNDS AND CORRESPONDING METHODS

This application claims priority benefit of U.S. Provisional Patent Application No. 63/101,848, filed May 18, 2020. The entire content of this application is hereby incorporated by reference herein in its entirety.

FIELD OF THE INVENTION

The present invention relates to Ibogaine derivatives and related methods. It more specifically relates to deutero- and fluoro-derivatives of Ibogaine and related methods.

BACKGROUND OF THE INVENTION

There have been reports of Ibogaine derivatives. U.S. Pat. No. 6,780,871, entitled "Methods and compositions for treating addiction disorders" allegedly reports the following: "A method for treating an addiction disorder (such as an addiction to or dependency on stimulants, nicotine, morphine, heroin, other opiates, amphetamines, cocaine, and/or alcohol) in a patient is disclosed. The method includes administering to the patient a first $\alpha_3\beta_4$ nicotinic receptor antagonist and administering to the patient a second $\alpha_3\beta_4$ nicotinic receptor antagonist. The second $\alpha_3\beta_4$ nicotinic receptor antagonist is different than the first $\alpha_3\beta_4$ nicotinic receptor antagonist, and the first $\alpha_3\beta_4$ nicotinic receptor antagonist and the second $\alpha_3\beta_4$ nicotinic receptor antagonist are administered simultaneously or non-simultaneously. Compositions which include a first $\alpha_3\beta_4$ nicotinic receptor antagonist and a second $\alpha_3\beta_4$ nicotinic receptor antagonist are also described. Examples of suitable $\alpha_3\beta_4$ nicotinic receptor antagonists for use in the present invention's methods and compositions include mecamylamine, 18-methoxycoronaridine, bupropion, dextromethorphan, dextrorphan, and pharmaceutically acceptable salts and solvates thereof. A method of evaluating a compound for its effectiveness in treating addiction disorders is also described." Abstract.

U.S. Pat. No. 9,592,239, entitled "Methods and compositions for ibogaine treatment of impulse control disorder, anxiety-related disorders, violence and/or anger, or regulating food intake" allegedly discusses the following: "This invention provides a method for treating anxiety-related disorder or impulse control disorder, regulating food intake, attenuating food cravings, or treating anger and/or violence and disorders associated therewith in a patient, comprising administering to the patient in need thereof a therapeutically effective amount of ibogaine, ibogaine derivative, or a pharmaceutically acceptable salt and/or solvate thereof" Abstract.

Despite the reports, there is still a need for novel Ibogaine-related compounds and corresponding methods.

SUMMARY OF THE INVENTION

In one aspect, the present invention provides a compound. The structure of the compound is shown as compound 1 in FIG. 1. The substituents for compound 1 are as follows: $R_1$ is H, D, OH, $CH_2OH$, $CD_2OH$, $CH_2CH_2OH$, $CH_2CD_2OH$, $CD_2CD_2OH$, $OCH_3$, $OCDH_2$, $OCD_2H$, $OCD_3$, $CH_2OCDH_2$, $CH_2OCD_2H$, $CH_2OCD_3$, $CH_2CH_2OCDH_2$, $CH_2CH_2OCD_2H$, $CH_2CH_2OCD_3$, $CH_2CD_2OCDH_2$, $CH_2CD_2OCD_2H$, $CH_2CD_2OCD_3$, $CD_2CD_2OCDH_2$, $CD_2$-$CD_2OCD_2H$, $CD_2CD_2OCD_3$, $CH_2CH_2OCH_2OCH_2OCH_3$, $CH_2CH_2OCH_2OCH_2CH_2OCDH_2$, $CH_2CH_2OCH_2OCH_2CH_2O$—$CD_2H$, $CH_2CH_2OCH_2OCH_2CH_2OCD_3$, $CH_2CH_2OCH_2OCH_2CH_2CD_2$-$OCD_3$, $CH_2CH_2OCH_2OCD_2CD_2OCD_3$, $CH_2CH_2OCH_2CH_2OCH_2CH_2OCH_3$, $CH_2CH_2O$—$CH_2CH_2OCH_2CH_2OCDH_2$, $CH_2CH_2OCH_2CH_2OCH_2CH_2OCD_2H$, $CH_2CH_2OCH_2CH_2OCH_2CH_2$—$OCD_3$, $CH_2CH_2OCH_2CH_2OCH_2CD_2OCD_3$, $CH_2CH_2OCH_2CH_2OCD_2CD_2OCD_3$, $OCF_3$, $CH_2OCF_3$, or $CD_2OCF_3$; $R_2$ is H, D, $CO_2H$, $CO_2R_{12}$ where $R_{12}$ is a pharmaceutically acceptable salt (e.g., sodium, fumaric, etc.), $CO_2CH_3$, $CO_2CH_2D$, $CO_2CHD_2$, $CO_2CD_3$, $CO_2CH_2CH_3$, $CO_2CH_2CD_3$, $CO_2CD_2CD_3$, $C(O)NH_2$, $C(O)NHCH_3$, $C(O)NHCD_3$, $C(O)N(CH_3)_2$, $C(O)N(CH_3)(CD_3)$, or $C(O)N(CD_3)_2$; $R_3$ is H, $C(O)OCH_3$, $C(O)OCD_3$, $C(O)CH_2CH_3$, $C(O)CH_2CD_3$, $C(O)CD_2CD_3$, $C(O)OCH_2CH_2OCH_3$, $C(O)OCH_2CH_2OCD_3$, $C(O)OCH_2CD_2OCD_3$, $C(O)OCD_2CD_2OCD_3$, or $C(O)OCF_3$; $R_4$ is H, D, F, Cl, Br, I, $CH_3$, $CF_3$, $CH_2CH_3$, $CO_2H$, $CO_2CH_3$, $C(O)NH_2$, $C(O)NHCH_3$, $C(O)N(CH_3)_2$, OH, $OCH_3$, $OCD_3$, or CN; $R_5$ is H, D, F, Cl, Br, I, $CH_3$, $CF_3$, $CH_2CH_3$, $CO_2H$, $CO_2CH_3$, $C(O)NH_2$, $C(O)NHCH_3$, $C(O)N(CH_3)_2$, OH, $OCH_3$, $OCD_3$, or CN; $R_6$ is H or D; $R_7$ is H or D; $R_8$ is H or D; $R_9$ is H or D; $R_{10}$ is H or D; $R_{11}$ is H or D; "n" is an integer selected from 1, 2, 3, 4, 5, 6, 7 and 8.

In another aspect, the present invention provides a method of treating an addiction disorder. The method comprises administration of compound 1 as discussed above.

In another aspect, the present invention provides a method of treating an anxiety-related disorder or impulse control disorder. The method comprises administration of compound 1 as discussed above.

DETAILED DESCRIPTION OF THE INVENTION

The compounds of the present invention typically include deuterium in an amount that is more than expected from isotopic abundance. This deuterium enrichment can be shown by inclusion of "D" in a chemical structure. Typically, in the case of deuterium enrichment, the amount of deuterium (e.g., where "D" is indicated), as opposed to protium or tritium, is more than 20 percent, more than 30 percent, more than 40 percent, more than 50 percent, more than 60 percent, more than 70 percent, more than 80 percent, more than 90 percent or more than 95 percent.

Figure 1:
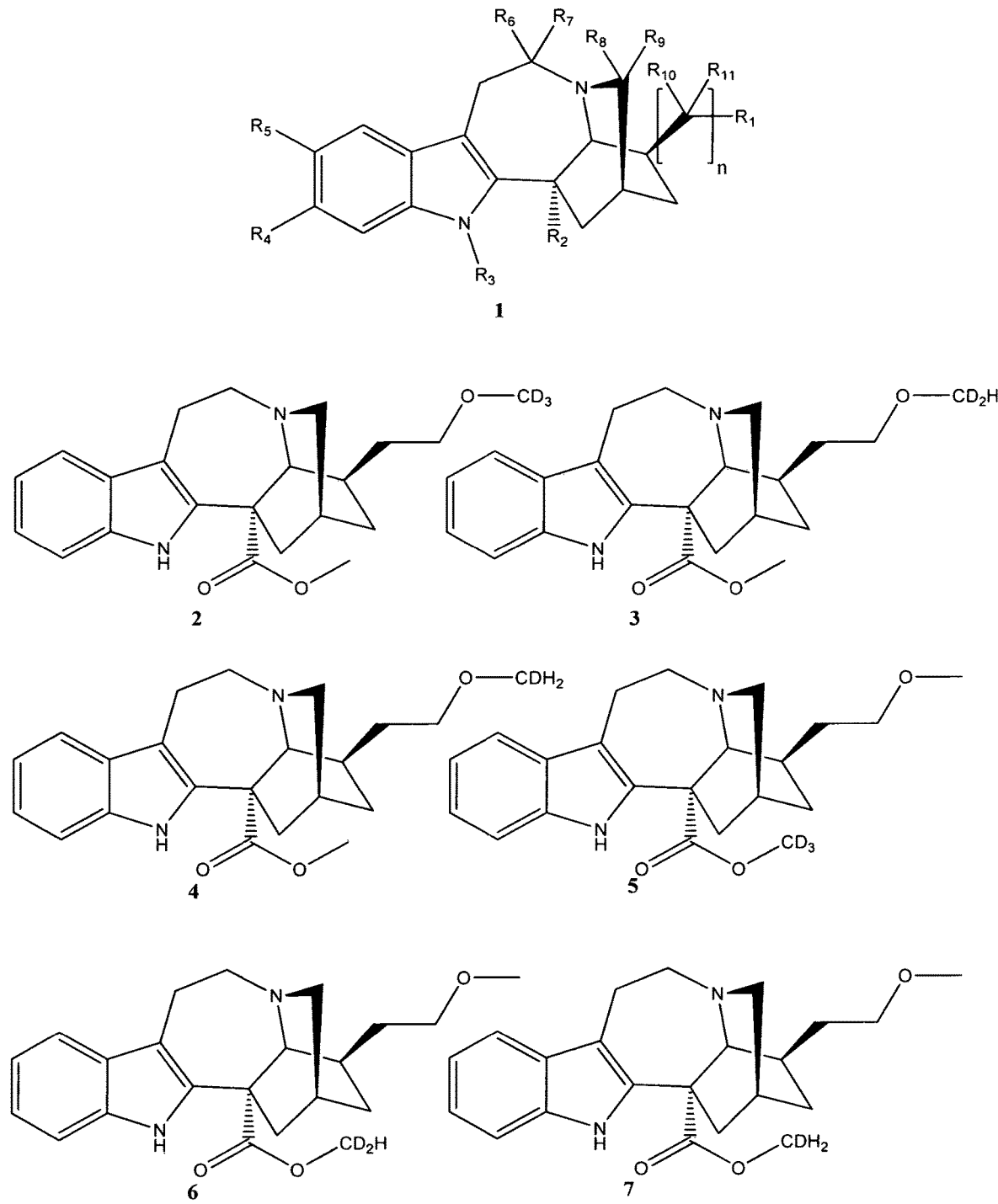
FIGS. 1-6 show examples of compounds according to the present invention.
Figure 2:
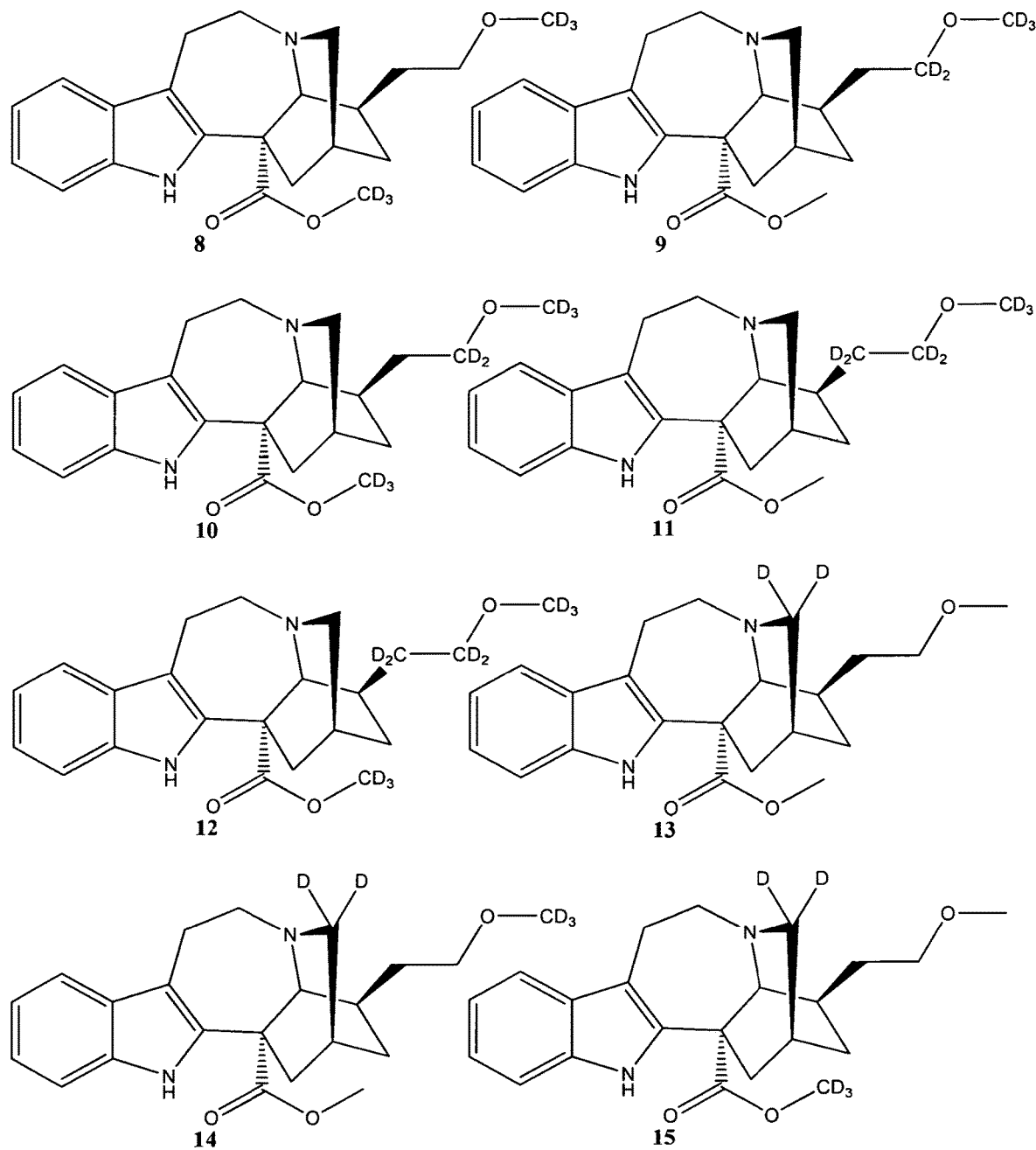
Figure 3:
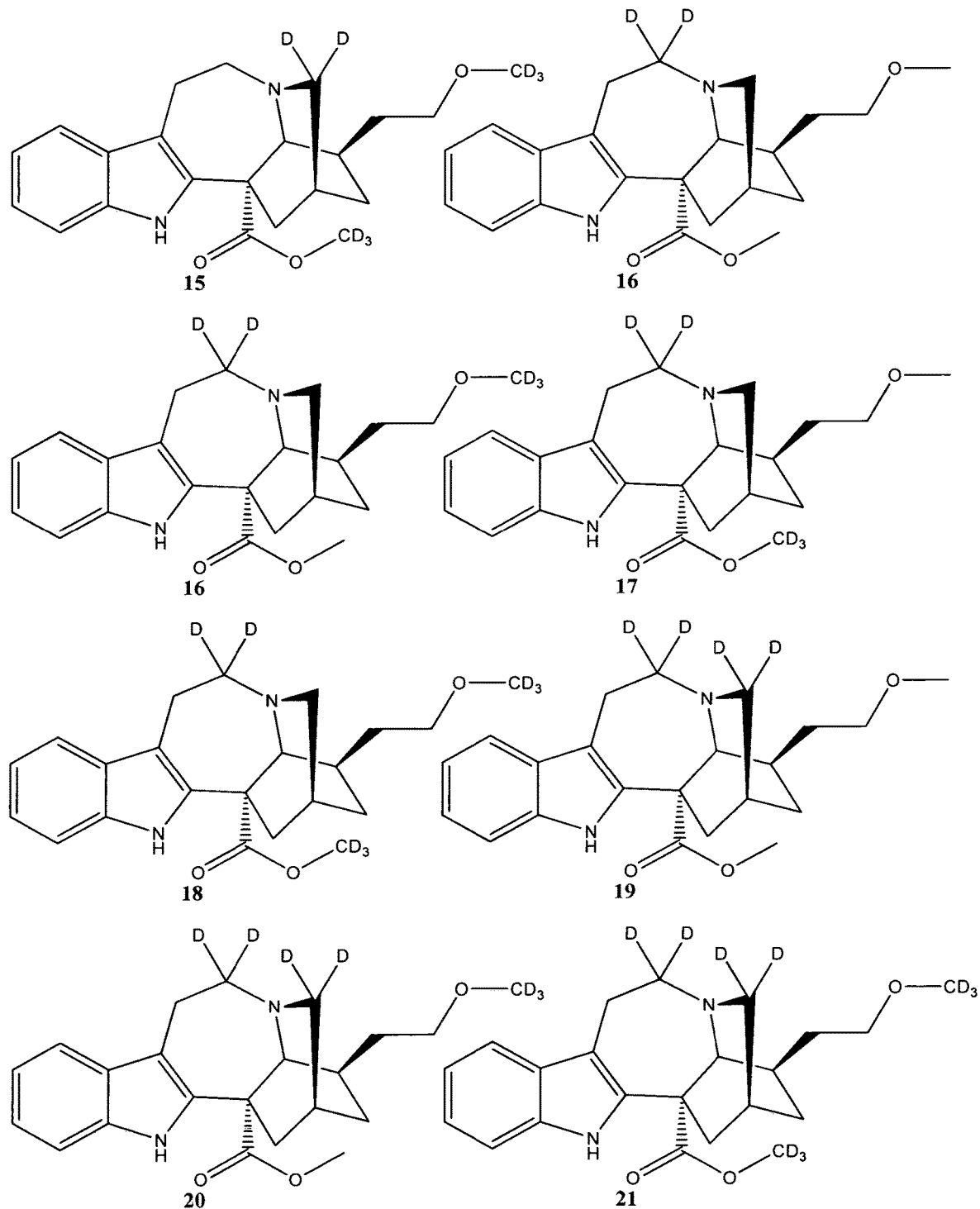
Figure 4:
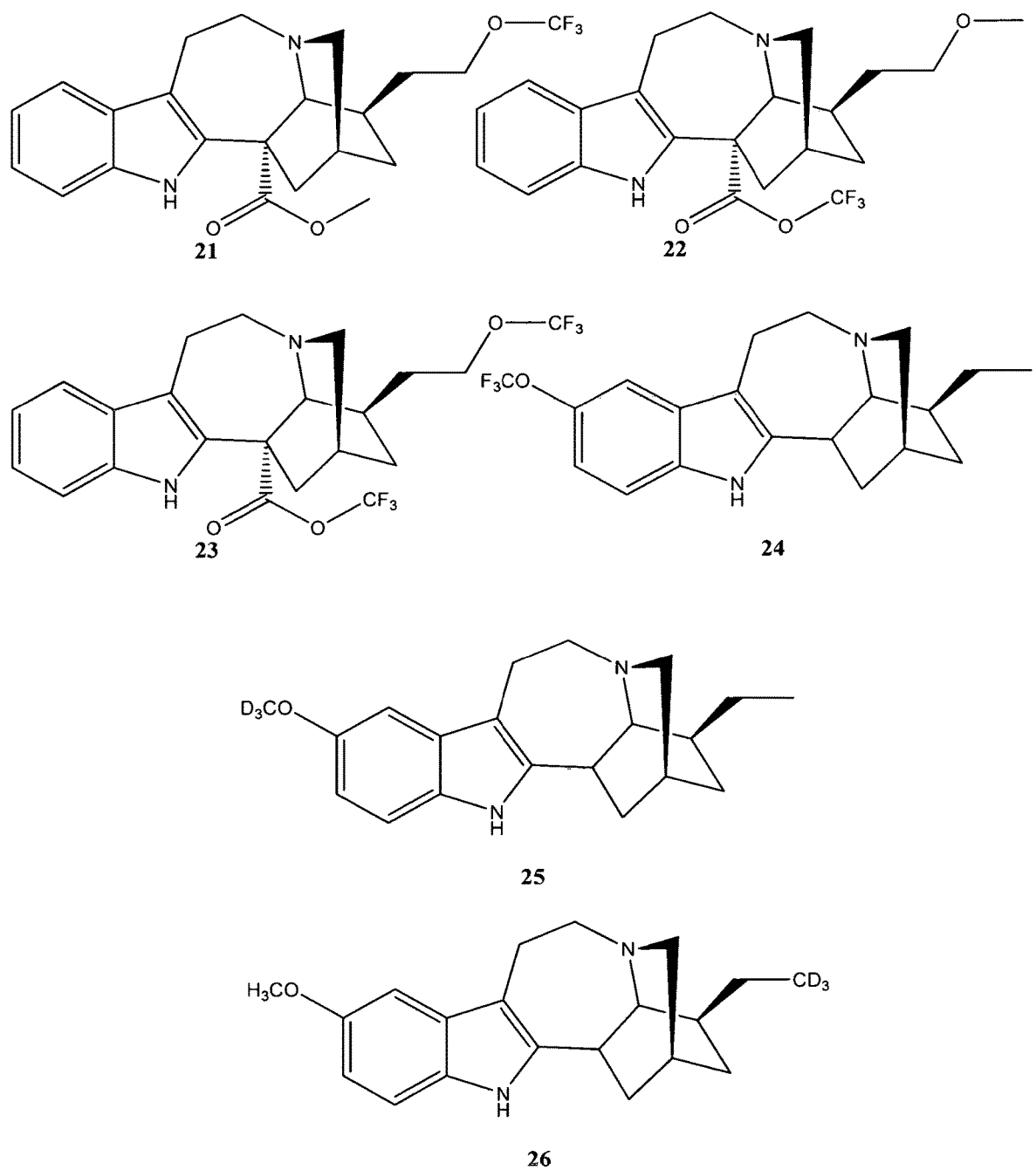
Figure 5:
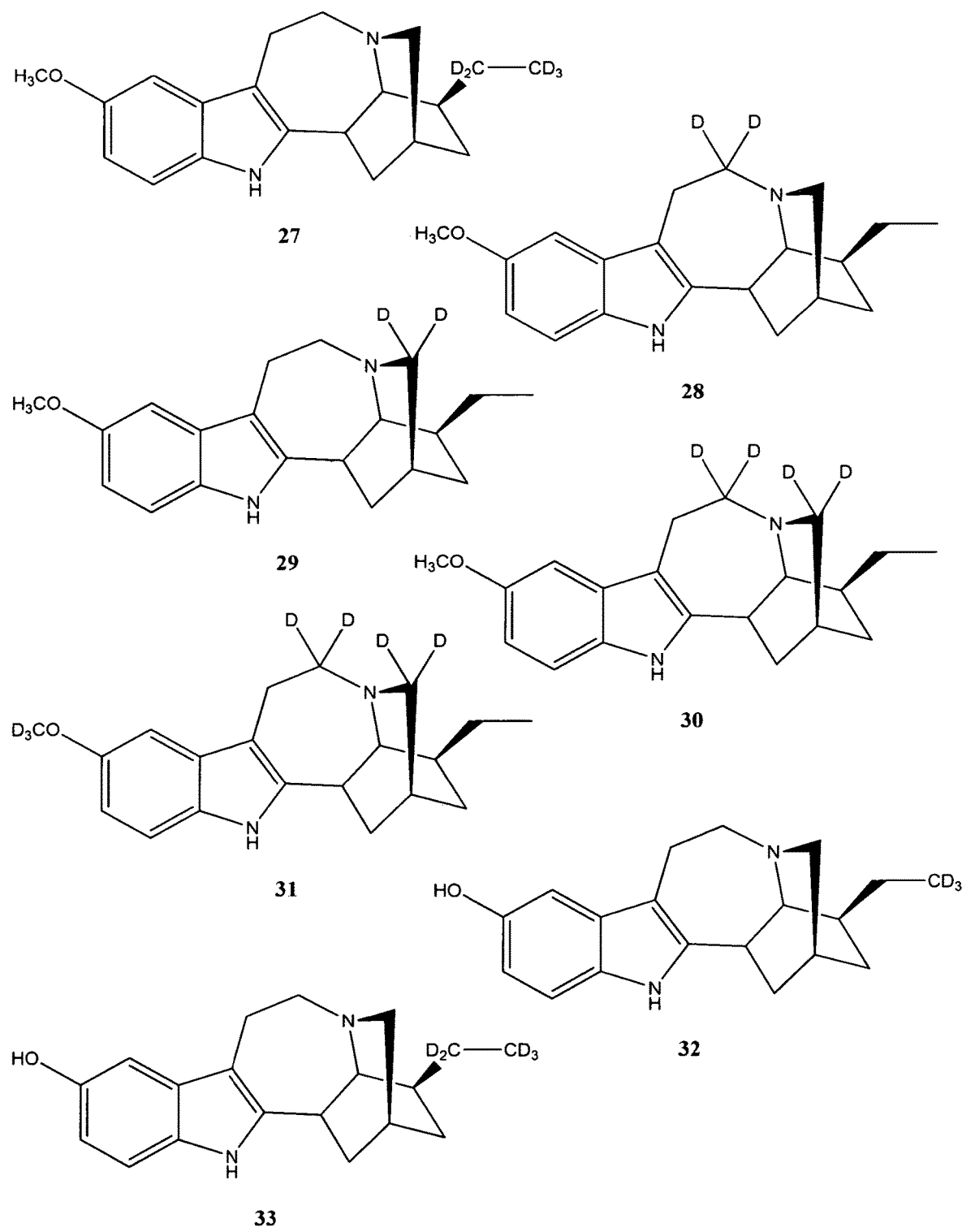
Figure 6:
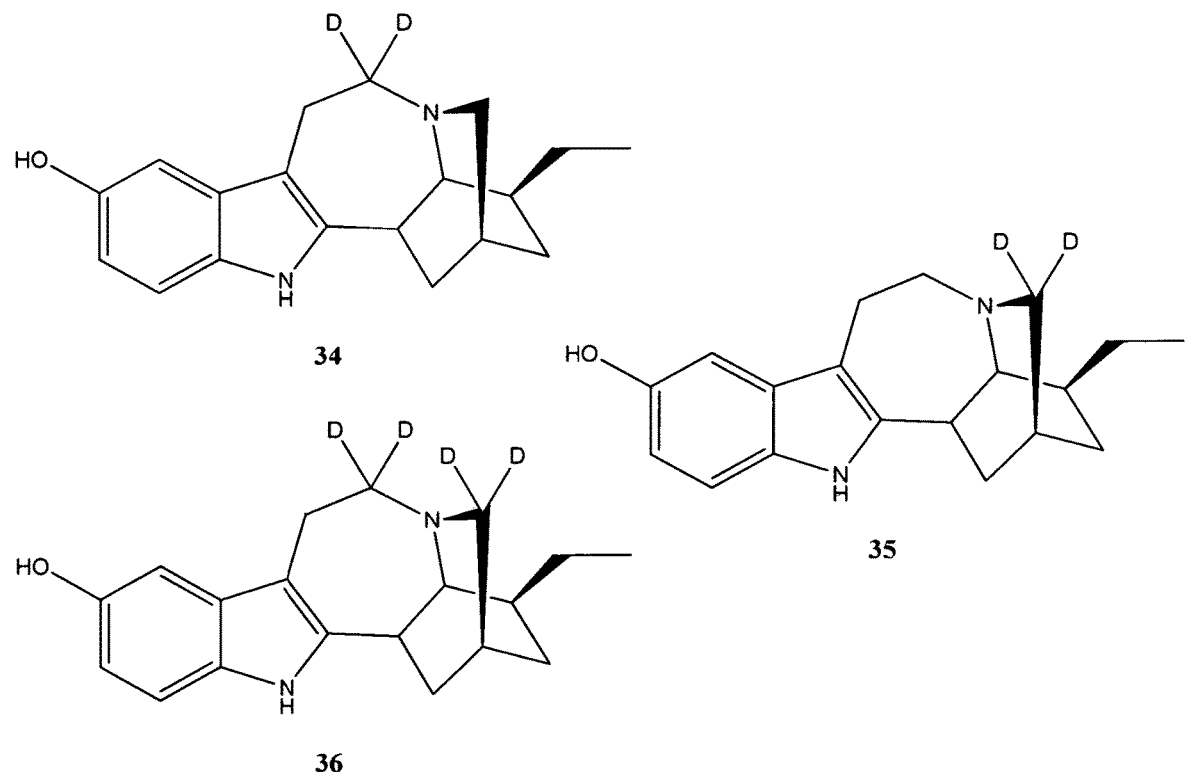

Examples of compounds of the present invention are shown in FIGS. 1-6. Regarding compound 1 in FIG. 1, substituents are as follows: $R_1$ is H, D, OH, $CH_2OH$, $CD_2OH$, $CH_2CH_2OH$, $CH_2CD_2OH$, $CD_2CD_2OH$, $OCH_3$, $OCDH_2$, $OCD_2H$, $OCD_3$, $CH_2OCDH_2$, $CH_2OCD_2H$, $CH_2OCD_3$, $CH_2CH_2OCDH_2$, $CH_2CH_2OCD_2H$, $CH_2CH_2OCD_3$, $CH_2CD_2OCDH_2$, $CH_2CD_2OCD_2H$, $CH_2CD_2OCD_3$, $CD_2CD_2OCDH_2$, $CD_2$-$CD_2OCD_2H$, $CD_2CD_2OCD_3$, $CH_2CH_2OCH_2OCH_2OCH_3$, $CH_2CH_2OCH_2OCH_2CH_2OCDH_2$, $CH_2CH_2OCH_2OCH_2CH_2O$—$CD_2H$, $CH_2CH_2OCH_2OCH_2CH_2OCD_3$, $CH_2CH_2OCH_2OCH_2CH_2CD_2$-$OCD_3$, $CH_2CH_2OCH_2OCD_2CD_2OCD_3$, $CH_2CH_2OCH_2CH_2OCH_2CH_2OCH_3$, $CH_2CH_2O$—$CH_2CH_2OCH_2CH_2OCDH_2$, $CH_2CH_2OCH_2CH_2OCH_2CH_2OCD_2H$, $CH_2CH_2OCH_2CH_2OCH_2CH_2$—$OCD_3$, $CH_2CH_2OCH_2CH_2OCH_2CD_2OCD_3$, $CH_2CH_2OCH_2CH_2OCD_2CD_2OCD_3$, $OCF_3$, $CH_2OCF_3$, or $CD_2OCF_3$; $R_2$ is H, D, $CO_2H$, $CO_2R_{12}$ where $R_{12}$ is a pharmaceutically acceptable salt (e.g., sodium, fumaric, etc.), $CO_2CH_3$, $CO_2CH_2D$, $CO_2CHD_2$, $CO_2CD_3$, $CO_2CH_2CH_3$, $CO_2CH_2CD_3$, $CO_2CD_2CD_3$, $C(O)NH_2$, $C(O)NHCH_3$, $C(O)NHCD_3$, $C(O)N(CH_3)_2$, $C(O)N(CH_3)(CD_3)$, or $C(O)N(CD_3)_2$; $R_3$ is H, $C(O)OCH_3$, $C(O)OCD_3$, $C(O)CH_2CH_3$, $C(O)CH_2CD_3$, $C(O)CD_2CD_3$, $C(O)OCH_2CH_2OCH_3$, $C(O)OCH_2CH_2OCD_3$, $C(O)OCH_2CD_2OCD_3$, $C(O)OCD_2CD_2OCD_3$, or $C(O)OCF_3$; $R_4$ is H, D, F, Cl, Br, I, $CH_3$, $CF_3$, $CH_2CH_3$, $CO_2H$, $CO_2CH_3$, $C(O)NH_2$, $C(O)NHCH_3$, $C(O)N(CH_3)_2$, OH, OM, $OCD_3$, or CN; $R_5$ is H, D, F, Cl, Br, I, $CH_3$, $CF_3$, $CH_2CH_3$, $CO_2H$, $CO_2CH_3$, $C(O)NH_2$, $C(O)NHCH_3$, $C(O)N(CH_3)_2$, OH, $OCH_3$, $OCD_3$, or CN; $R_6$ is H or D; $R_7$ is H or D; $R_8$ is H or D; $R_9$ is H or D; $R_{10}$ is H or D; $R_{11}$ is H or D; "n" is an integer selected from 1, 2, 3, 4, 5, 6, 7 and 8.

Compounds of the present invention can be used to treat a variety of disorders, including, without limitation, the following: an addiction disorder (e.g., addiction to or dependency on stimulants, nicotine, morphine, heroin, other opiates, amphetamines, cocaine and/or alcohol); an anxiety-related disorder or impulse control disorder, regulating food intake (e.g., obesity), attenuating food cravings, or treating anger and/or violence and disorders associated therewith.

Compounds of the present invention can be synthesized using methods known to one of ordinary skill in the art. Nonlimiting examples of such methods, using known compounds and intermediates—as seen and discussed in U.S. Pat. Nos. 6,780,871, 8,993,559, 9,592,239, 6,211,360 and Bornmann, et al., *J. Org. Chem.*, 57:1752 (1992)—can be found in the following articles: Miyashita, M.; Sasaki, M.; Hattori, I.; Sakai, M.; Tanino, K. Science 2004, 305, 495; Foster, A. B. Trends Pharmacol. Sci. 1984, 5, 524; Kushner, D. J.; Baker, A.; Dunstall, T. G. Can. J. Physiol. Pharmacol. 1999, 77, 79; Harbeson, S. L.; Tung, R. D. Annu. Rep. Med. Chem. 2011, 46, 403; Meanwell, N. A. J. Med. Chem. 2011, 54, 2529; Phillips, D. H.; Potter, G. A.; Horton, M. N.; Hewer, A.; Crofton-Sleigh, C.; Jarman, M.; Venitt, S. Carcinogenesis 1994, 15, 1487; Jarman, M.; Poon, G. K.; Rowlands, M. G.; Grimshaw, R. M.; Horton, M. N.; Potter, G. A.; McCague, R. Carcinogenesis 1995, 16, 683; Mutlib, A. E.; Gerson, R. J.; Meunier, P. C.; Haley, P. J.; Chen, H.; Gan, L. S.; Davies, M. H.; Gemzik, B.; Christ, D. D. et al. Toxicol. Appl. Pharmacol. 2000, 169, 102; Mutlib, A. E.; Gerson, R. J.; Meunier, P. C.; Haley, P. J.; Chen, H.; Gan, L. S.; Davies, M. H.; Gemzik, B.; Christ, D. D. et al. Toxicol. Appl. Pharmacol. 2000, 169, 102; Maltais, F.; Jung, Y. C.; Chen, M.; Tanoury, J.; Perni, R. B.; Mani, N.; Laitinen, L.; Huang, H.; Liao, S.; Gao, H. et al. J. Med. Chem. 2009, 52, 799; Katsnelson, A. Nature Med. 2013, 19, 656; Atzrodt, J.; Derdau, V.; Fey, T.; Zimmermann, J. Angew. Chem. Int. Ed. 2007, 46, 7744; Atzrodt, J.; Derdau, V. J. Label. Compd. Radiopharm. 2010, 53, 67; Kluger, R. J. Org. Chem. 1964, 29, 2045; Paulsen, P. J.; Cooke, W. D. Anal. Chem. 1963, 35, 1560; Yung, C. M.; Skaddan, M. B.; Bergman, R. G. J. Am. Chem. Soc. 2004, 126, 13033; Skaddan, M. B.; Yung, C. M.; Bergman, R. G. Org. Lett. 2004, 6, 11; Heys, R. J. Chem. Soc., Chem. Commun. 1992, 68; Shu, A. Y. L.; Chen, W.; Heys, J. R. J. Organomet. Chem. 1996, 524, 87; Ma, S.; Villa, G.; Thuy-Boun, P. S.; Horns, A.; Yu, J.-Q. Angew. Chem. Int. Ed. 2014, 53, 734; Zhou, J.; Hartwig, J. F. Angew. Chem. Int. Ed. 2008, 47, 578; Takahashi, M.; Oshima, K.; Matsubara, S. Chem. Lett. 2005, 34, 19; Neubert, L.; Michalik, D.; Balm, S.; Imm, S.; Neumann, H.; Atzrodt, J.; Derdau, V.; Holla, W.; Beller, M. J. Am. Chem. Soc. 2012, 134, 12239; Sajiki, H.; Ito, N.; Esaki, H.; Maesawa, T.; Maegawa, T.; Hirota, K. Tetrahedron Lett. 2005, 46, 6995; Sajiki, H.; Aoki, F.; Esaki, H.; Maegawa, T.; Hirota, K. Org. Lett. 2004, 6, 1485. The preceding articles and patents are incorporated-by-reference into this document for all purposes. For the synthesis of trifluoromethyl ethers and related compounds, see, for example: Leroux et al., *Beilstein J Org. Chem.* 2008, 4, No. 13, which is incorporated-by-reference into this document for all purposes.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, microcapsules and the like. They may also be manufactured in the form of sterile solid compositions which can be dissolved or suspended in sterile injectable medium immediately before use. They may contain suspending or dispersing agents known in the art. Where microcapsules are employed, they can be readily prepared by conventional microencapsulation techniques, such as those disclosed in, for example, Encyclopedia of Chemical Technology, 3rd edition, volume 15, New York: John Wiley and Sons, pp. 470-493 (1981), which is hereby incorporated by reference.

Preferably, a compound or composition according to the present invention is administered in amounts that are effective to treat a patient's disorder. Illustratively, a compound or composition can be administered in an amount from about 0.01 to about 10 mg/kg of the patient's body weight per day. In certain cases, the compound or composition can be administered in an amount from about 0.02 to about 5 mg/kg of the patient's body weight per day or in an amount from about 0.1 to about 5 mg/kg of the patient's body weight per day.

The invention claimed is:

1. A compound, wherein the compound is of the following structure:

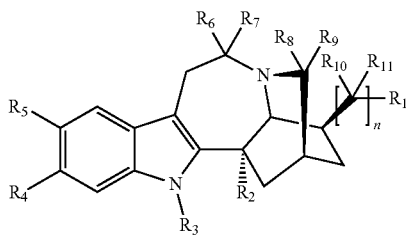

wherein, $R_1$ is H; $R_2$ is H; $R_3$ is H; $R_4$ is H; $R_5$ is $OCD_3$; $R_6$ is H; $R_7$ is H; $R_8$ is H; $R_9$ is H; $R_{10}$ is H; $R_{11}$ is H; "n" is an integer selected from 1, 2, 3, 4, 5, 6, 7 and 8.

2. A method of treating nicotine addiction comprising administration of a compound according to claim 1.

3. A method of treating food cravings comprising administration of a compound according to claim 1.

* * * * *